(12) United States Patent
Raoof et al.

(10) Patent No.: US 7,820,722 B2
(45) Date of Patent: *Oct. 26, 2010

(54) PERMEATION ENHANCERS

(75) Inventors: Araz A. Raoof, Cabinteely (IE); Mangaraju Gudipati, Yardley, PA (US)

(73) Assignee: Merrion Research III Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 10/145,194

(22) Filed: May 13, 2002

(65) Prior Publication Data

US 2003/0036568 A1 Feb. 20, 2003

Related U.S. Application Data

(60) Provisional application No. 60/290,436, filed on May 11, 2001.

(51) Int. Cl.
A61K 47/12 (2006.01)
A61K 31/727 (2006.01)
(52) U.S. Cl. .......................... 514/784; 514/772; 514/56
(58) Field of Classification Search ................. 514/772, 514/784, 56; 562/30, 606
See application file for complete search history.

(56) References Cited

U.S. PATENT DOCUMENTS

| | | | |
|---|---|---|---|
| 4,525,339 A | 6/1985 | Behl et al. | |
| 4,656,161 A | 4/1987 | Herr | |
| 4,789,547 A | 12/1988 | Song et al. | 424/449 |
| 5,190,748 A | 3/1993 | Bachynsky et al. | |
| 5,229,130 A | 7/1993 | Sharma et al. | |
| 5,288,497 A | 2/1994 | Stanley et al. | 424/440 |
| 5,541,155 A | 7/1996 | Leone-Bay et al. | |
| 5,650,386 A | 7/1997 | Leone-Bay et al. | |
| 5,714,477 A | 2/1998 | Einarsson | |
| 5,854,281 A | 12/1998 | Uekama et al. | 514/468 |
| 5,863,555 A | 1/1999 | Heiber et al. | 424/435 |
| 5,912,009 A | 6/1999 | Venkateshwaran et al. | 424/448 |
| 5,952,000 A | 9/1999 | Venkateshwaran et al. | 424/448 |
| 5,977,175 A | 11/1999 | Lin | |
| 6,001,390 A | 12/1999 | Yum et al. | 424/448 |
| 6,200,602 B1 | 3/2001 | Watts et al. | |
| 6,262,161 B1 | 7/2001 | Betso et al. | |
| 6,264,981 B1 * | 7/2001 | Zhang et al. | 424/451 |
| 6,326,360 B1 | 12/2001 | Kanazawa et al. | |
| 6,379,960 B1 | 4/2002 | Popoff et al. | 435/375 |

FOREIGN PATENT DOCUMENTS

| | | |
|---|---|---|
| EP | 0376 534 A1 | 7/1990 |
| EP | 0 497 162 | 8/1992 |
| EP | 0 517211 | 12/1992 |
| EP | 0 580 074 A1 | 1/1994 |
| GB | 953 626 | 3/1964 |
| JP | 51031687 | 3/1976 |
| JP | 59 073 600 | 4/1984 |
| JP | 2-207018 A | 8/1990 |
| JP | 2-282327 A | 11/1990 |
| JP | 03 275 633 | 12/1991 |
| JP | 6-40949 A | 2/1994 |
| JP | 11-35458 A | 2/1999 |
| JP | 2004-4529953 | 9/2004 |
| RU | 2 068 689 | 11/1996 |
| WO | WO 8404674 A1 | 12/1984 |
| WO | WO 9321907 | 11/1993 |
| WO | WO 9522319 | 8/1995 |
| WO | WO 9534294 | 12/1995 |
| WO | WO 9705903 | 2/1997 |
| WO | WO 99/02120 * | 1/1999 |
| WO | WO 99/02485 * | 1/1999 |
| WO | WO 9902120 * | 1/1999 |
| WO | WO 99/45934 A1 | 9/1999 |
| WO | WO 00/22909 * | 4/2000 |
| WO | WO 0022909 * | 4/2000 |
| WO | WO 00/50012 | 8/2000 |
| WO | WO 02/092070 A1 | 11/2002 |

OTHER PUBLICATIONS

Pharmaceutical Research, 1997, 14(2), 1772-1779.*
Critical Reviews in Therapeutic Drug Carrier Systems, 1990, 7(1), 1-133.*
Critical Reviews in Therapeutic Drug Carrier Systems, 1991, 8(2), 91-192.*
Brayden et al, Pharmaceutical Research, 1997, 14(12), 1772-1779.*
Muranishi, Critical Reviews in Therapeutic Drug Carrier Systems, 1990, 7(1), 1-133.*
Lee et al, Critical Reviews in Therapeutic Drug Carrier Systems, 1991, 8(2), 91-192.*
Brayden et al, Pharmaceutical Research, 1997, 14(12), 1772-1779.*
Aungst, B.J. et al., Enhancement of the Intestinal Absorption of Peptides and Non-peptides, J. of Controlled Release (1996), 41:19-31.
Lindmark, T. et al., Mechanism of Aborption Enhancement in Humans After Rectal Adminstration of Ampicillin in Suppositories Containing Sodium Caprate, Pharmaceutical Research (1997), 14: 930-935.

(Continued)

Primary Examiner—Shaojia Anna Jiang
Assistant Examiner—Ganapathy Krishnan
(74) Attorney, Agent, or Firm—Myers Bigel Sibley & Sajovec P.A.

(57) ABSTRACT

A pharmaceutical composition comprising a drug and a permeation enhancer that comprises a multi-carbon backbone having a functional group and also one or more side chains which have one or more carbon atoms and, optionally, one or more functional groups.

21 Claims, No Drawings

OTHER PUBLICATIONS

Anderberg, E.K. et al., Sodium Caprate Elicits Dilatations in Human Intestinal Tight Junctions and Enhances Drug Absorption by the Paracellular Route, Pharmaceutical Research (1993), 10: 857-864.

Yeh, P. et al., Effect of Medium-chain Glycerides on Physiological Properties of Rabbit Intestinal Epithelium in Vitro, Pharmaceutical Research (1994), 11: 1148-1154.

Artursson, P., Epithelial Transport of Drugs in Cell Culture. I: A Model for Studying the Passive Diffusion of Drugs over Intestinal Absorbative (Caco-2) Cells, J. Pharmaceutical Studies (1990), 79: 476-482.

Doluisio, J.T. et al., Drug Absorption I: An In Situ Rat Gut Technique Yielding Realistic Asorption Rates, J. Pharmaceutical Studies (1969), 59: 1196-1200.

Brayden, D. et al., Heparin Absorption Across the Intestine: Effects of Sodium N-[8-(2-Hydroxybenzoyl)Amino]Caprylate in Rat In Situ Intestinal Instillations and in Caco-2 Monolayers, Pharmaceutical Research (1997), 14: 1772-1779.

Cumming, K.I. and A.J. Winfield, In Vitro Evaluation of a Series of Sodium Carboxylates as Dermal Penetration Enhancers, Int. J. Pharm. (1994), 108: 141-148.

Tomita, M. et al., Enhancement of Colonic Drug Absorption by the Paracellular Permeation Route, Pharmaceutical Research (1988), 5: 341-346.

Gennaro, A. R., Remington: The Science and Practice of Pharmacy (1995), 1618.

Oda et al., Proc. Int'l Symp. Control. Rel. Bioact. Mater. 24 (1997) 283-284.

Bennett, D. et al., Pulmonary Delivery of Detirelix Intratracheal Instillation and Aerosol Inhalation in the Briefly Anesthetized Dog, Pharmaceutical Research (1994), vol. 11, No. 7, 1048-1054.

Cumming et al. "In vitro evaluation of a series of sodium carboxylates as dermal penetration enhancers", *International J. of Pharmaceutics* 108:141-148 (1994).

Supplementary European Search Report corresponding to European Application No. 02731786.6 mailed Jun. 6, 2008.

Aungst. "Structure/Effect Studies of Fatty Acid Isomers as Skin Penetration Enhancers and Skin Irritants" *Pharmaceutical Research* 6(3):244-247 (1989).

Notice of Reasons for Rejections and English translation for Japanese Patent Application No. 2002-588986, mailed Feb. 3, 2009 (6 pages).

Schneider et al. "Evaluation of Drug Penetration into Human Skin Ex Vivo Using Branched Fatty Acids and Propylene Glycol" *International Journal of Pharmaceutics* 145:187-196 (1996).

International Journal of Pharmaceutics, 1994, vol. 108(2), pp. 141-148 In Vitro Evaluation of a Series of Sodium Carboxylates as Dermal Penetration Enhancers, K.I. Cumming and A.J. Winfield.

* cited by examiner

```
SEQUENCE LISTING

<160> NUMBER OF SEQ ID NOS: 1

<210> SEQ ID NO 1
<211> LENGTH: 20
<212> TYPE: DNA
<213> ORGANISM: Artificial
<220> FEATURE:
<223> OTHER INFORMATION: human TNF-alpha antisense oligonucleotide

<400> SEQUENCE: 1
gctgattaga gagaggtccc                                              20
```

PERMEATION ENHANCERS

This application is related to and claims priority to U.S. Provisional Application No. 60/290,436, filed May 11, 2001.

FIELD OF THE INVENTION

The present invention relates to permeation enhancers that are useful in the administration of a drug.

Drug delivery systems generally involve a permeation step followed by absorption into the circulatory system. For example, a drug can be applied through the skin by use of a transdermal patch which comprises a drug and a film or fabric and which is adhered to the outer skin of the patient. Drugs are delivered also across a mucous membrane or other cellular membrane (collectively "transmucosal"), for example, by: (A) aerosol delivery of the drug to the nose or lungs; (B) oral ingestion of the drug followed by permeation through the gastrointestinal wall; and (C) the dissolution of lozenges or pills held between the cheek and gum or under the tongue followed by transport through the membranes of the mouth.

During the early development of transdermal delivery systems, investigators found that the oily, hydrophobic nature of the skin reduces significantly the absorption rate of aqueous drug solutions or dispersions. Thus, the natural barrier properties of skin, which protect the body against the ingress of foreign substances, act also as barriers to applied drugs, thereby reducing their rate of permeation and ultimately their bioavailability. Problems are encountered also in delivering drugs in a satisfactory way by transmucosal means. The rate of drug permeation is an important factor in achieving bioavailability and pharmaceutically useful concentrations of the drug at the target membrane. It is not surprising that considerable effort has been dedicated toward the objective of enhancing the rate of drug permeation through the skin or by transmucosal means. Examples of such efforts are summarized below.

REPORTED DEVELOPMENTS

U.S. Pat. No. 5,854,281 (Uekama, et al.) teaches the use of straight chain fatty acids, salts, and esters thereof to enhance the percutaneous permeability of prostaglandin. U.S. Pat. Nos. 5,952,000 and 5,912,009 (Venkateshwaran, et al.) disclose drug delivery systems that are enhanced by the presence of a fatty acid ester of lactic acid (or salts thereof) and a fatty acid ester (or salts thereof) of glycolic acid respectively. The use of glycerides of fatty acids to enhance the skin permeation of a biologically active pergolide is disclosed in U.S. Pat. No. 6,001,390 (Yum, et al.). U.S. Pat. No. 4,789,547 teaches the enhancement of drug permeation through the skin by a saturated or unsaturated fatty acid in a solvent such as propylene glycol. Published PCT application WO00/22909 discloses oral delivery systems for pharmaceutical or other biologically active substances wherein the pharmaceutical or other substance is coated or complexed with a carboxylic acid to enable the substance to transit the stomach and to be absorbed in the intestine. The coating or complexing is achieved by means of co-precipitation from an acidic solution of the active substance and carboxylic acid, which is described as having from nine to 30 carbon atoms in a straight or branched chain, saturated or unsaturated, acyclic or cyclic structure and further substituted or unsubstituted with functional groups such as steroid rings, phenyl groups and the like. WO00/22909 discloses specific examples of complexes formed from the straight chain, saturated or unsaturated or steroidal carboxylic acids, dodecanoic acid, tetradecanoic acid, hexadecanoic acid, octadecanoic acid, oleic acid. palmitoleic acid, ricinoleic acid and fusidic acid.

Investigators continue to seek ways to administer safely and effectively drugs by transmucosal or transdermal routes. Obstacles to these goals are the complexity and variability in the properties of the various types of membranes and the skin. Furthermore, candidate drugs possess a wide range of molecular size, shape, and chemical properties. Variations in the structure and chemistry of both the drug and the skin and mucous membranes contribute to the unpredictable nature of drug delivery. In light of the recognized need to overcome the natural barrier properties of bodily membranes and skin in achieving drug bioavailability, the present invention relates to the provision of a class of compounds that enhance the permeation of drugs for delivery to a patient.

SUMMARY OF THE INVENTION

In accordance with the present invention, there is provided a composition comprising a drug and a compound which is effective in enhancing the bioavailability of said drug and which comprises a multi-carbon backbone having a functional group and also one or more side chains which have one or more carbon atoms and, optionally, one or more functional groups. A preferred class of bioavailability-enhancing compounds comprises a compound of Formula I below.

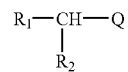

Formula I wherein, Q is
(1) a partially or completely neutralized —COOH, or
(2) a partially or completely neutralized —SO$_3$H, or
(3) a mono- or di-substituted alkyl or alkenyl group having one to about twelve carbon atoms, the substituent(s) thereof being a partially or completely neutralized —COOH or partially or completely neutralized —SO$_3$H;

R$_1$ and R$_2$ are independently
(1) an unsubstituted alkyl or alkenyl group having one to about twelve carbon atoms, or
(2) a substituted alkyl or alkenyl group having one to about twelve carbon atoms, the substituent thereof being selected from the group consisting of
  (i) partially or completely neutralized —COOH,
  (ii) partially or completely neutralized —SO$_3$H,
  (iii) —NH$_2$,
  (iv) —CONH$_2$; and
  (v) —OH.

Another aspect of the present invention comprises a method of treating a condition in a patient comprising administering to the patient a composition comprising a pharmaceutically effective amount of a drug for treating the condition and a permeation enhancer of Formula I in an enhancing-effective amount.

As explained below, a particular advantage of the present invention is that it provides to the medical and pharmaceutical professions a class of compounds that enhance the permeation of said drug into and through the intestinal barrier of a subject and that have widely different hydrophilic-hydrophobic properties. This enables the user to tailor-make an enhancer compound that has hydrophilic/hydrophobic properties that are particularly effective for increasing the permeation properties of a selected drug.

DETAILED DESCRIPTION OF THE INVENTION

As mentioned above, the composition of the present invention comprises a drug, a compound that is characterized herein as a permeation enhancer, and, optionally, a vehicle. In selecting a permeation enhancer from among the compounds represented by Formula I, consideration is given to both the nature of the drug employed and to the tendency of the target membrane or skin to absorb the drug. As will become evident from the following discussion, there is included within the class of enhancer compounds of the present invention compounds that have a wide range of hydrophobic-hydrophilic properties and that may be described as branched chain compounds.

The compounds of Formula I comprise a multi-carbon backbone having a functional group and also a side chain(s) which has one or more carbon atoms and, optionally, one or more functional groups. The compounds are therefore distinguished from the straight chain carboxylic acids reported in the literature as having permeation enhancer properties. Each of $R_1$ and $R_2$ of Formula I represents an unsubstituted alkyl or unsubstituted alkenyl group having 1 to about 12 carbon atoms or a substituted alkyl or substituted alkenyl group having 1 to about 12 carbon atoms, or one of $R_1$ or $R_2$ can be a substituted alkyl or substituted alkenyl group having 1 to about 12 carbon atoms and the other an unsubstituted alkyl or unsubstituted alkenyl group. Each of $R_1$ and $R_2$ of Formula I may be a straight chain, branched, or cyclo-aliphatic group.

In addition, one of $R_1$ or $R_2$ can be an alkyl group and the other an alkenyl group. Examples of alkyl groups are methyl, ethyl, isopropyl, hexyl, octyl, decyl, and dodecyl. Preferably, the alkyl group has at least about 4 to about 12 carbon atoms. Examples of alkenyl groups are octenyl, pentenyl, and dodecenyl. Preferably, the alkenyl group has at least about 4 to about 12 carbon atoms.

Also, in preferred form, the sum of the carbon atoms in $R_1$ and $R_2$ is at least about 16. In a particularly preferred form of the invention, $R_1$ is alkyl and $R_2$ is alkyl. For those enhancers in which $R_1$ and/or $R_2$ includes a substituted alkyl or substituted alkenyl group, it is preferred that the substituent thereof is a hydroxyl group.

As set forth in Formula I, enhancer compounds useful in the present invention can include a partially or completely neutralized —COOH or —SO$_3$H group. As used herein, the term "neutralized" means the reaction product of the carboxylic acid or sulfonic acid with a base that is present in an amount sufficient to react with all of the acid. As used herein, the term "partially neutralized" means the reaction product of the carboxylic or sulfonic acid with an amount of base that reacts with less than all of the acid, but with at least about 50% of the acid. Examples of bases that can be used are sodium hydroxide, sodium carbonate, potassium hydroxide, magnesium hydroxide, calcium hydroxide, ammonium hydroxide, and trialkyl amine. Preferably, -Q of Formula I is the sodium salt of —COOH. For those enhancers where -Q of Formula I is a substituted alkyl or substituted alkenyl group, the following are examples of such groups: methyl, hexyl, octyl, and dodecyl. Preferably, the total number of carbon atoms in the alkyl or alkenyl group is about one to about 12, with an alkyl group being preferred.

In a preferred group of compounds of Formula I, $R_1$ is $C_6$-$C_{12}$ alkyl, $R_2$ is $C_4$-$C_{10}$ alkyl, and -Q is neutralized —COOH. Particularly preferred permeation enhancers are compounds represented by Formula I wherein $R_1$ is $C_{6-8}$ alkyl, $R_2$ is $C_{8-10}$ alkyl, and -Q is —COONa.

A preferred enhancer compound useful in the present invention comprises the sodium salt of a carboxylic acid of Formula I in which $R_1$ is an alkyl group having eight carbon atoms ($C_8H_{17}$) and $R_2$ is an alkyl group having six carbon atoms ($C_6H_{13}$). An additionally preferred enhancer compound comprises the sodium salt of a carboxylic acid of Formula I in which $R_1$ is an alkyl group having ten carbon atoms ($C_{10}H_{21}$) and $R_2$ is an alkyl group having eight carbon atoms ($C_8H_{17}$).

The enhancer compounds useful in the present invention can include at least one chiral center. When the enhancer compound includes a chiral center, it and may be used as a racemic mixture of optical isomers, or optionally as the essentially pure D or L isomers of the enhancer compound.

Enhancer compounds within the scope of the present invention are known. It will be recognized that preparation of an enhancer compound is well within the purview of one of ordinary skill in the art. Speaking generally, the enhancer carboxylic acids useful in the present invention can be prepared according to known preparative methods. Non-limiting examples of preparative methods include the oxidative cleavage of an appropriately unsaturated hydrocarbon with a strong oxidizing agent and the saponification of a corresponding ester. A non-limiting example of a typical ester is the glyceride of the desired acid.

Neutralization of a carboxylic acid or sulfonic acid with an alkali such as sodium hydroxide is generally carried out by adding the alkali to a stirred solution of the acid dissolved in water or a mixture of water and alcohol. The degree of neutralization is monitored by changes in pH as measured by conventional means.

The enhancer of Formula I can be mono-functional or multi-functional. The degree of functionality and length of the carbon chain are related to the hydrophilic-hydrophobic (lipophilic) nature of the enhancer compounds. In general, the higher the degree of functionality, the more hydrophilic is the compound. Also, speaking generally, the greater the number of carbon atoms in the compound, the more hydrophobic the compound is. Improved drug delivery can be achieved when the hydrophobic-hydrophilic balance of the enhancer is matched appropriately to the drug and to the targeted tissue. Selecting —$R_1$, —$R_2$ and -Q with relatively long carbon chains can provide enhancers having a relatively high degree of hydrophobicity. In contrast, enhancers with relatively short carbon chains and with multi-functional groups have a relatively high degree of hydrophilicity.

The composition of the present invention can comprise an enhancer compound of Formula I or a mixture of two or more of the said compounds. Also, the composition of the present invention may comprise one or more enhancer compound(s) of Formula I in admixture with one or more other enhancers, for example, a straight chain fatty acid, an ester or salt thereof, or other compounds that promote the formation of liposomes or a micro emulsion. When another enhancer compound(s) is used, it may be present in a weight ratio of up to about 99 parts of the additional enhancer for each part of the enhancer of Formula I, for example, a weight ratio of an additional enhancer: the enhancer of Formula I from about 99:1 to about 1:99. In preferred form, in a composition comprising an admixture of one or more enhancer compounds of the present invention (those of Formula I) and another enhancer compound(s), the enhancer compound(s) of Formula I comprises by weight at least about 50% of the enhancer compounds present; more preferably the enhancer compound(s) of Formula I comprises about 70% of the enhancer compounds present.

When an enhancer compound of the present invention is mixed with another enhancer compound(s) in formulations used in connection with delivery of a drug comprising an oligonucleotide or polynucleotide, typically the enhancer compound(s) of Formula I comprises, by weight, at least about 10% of the enhancer compounds present in the formulation.

The composition of the present invention comprises also a drug, for example, a chemical compound that has prophylactic, therapeutic, or diagnostic properties and which is used in the treatment of humans or other animals. The composition can comprise a mixture of two or more drugs.

It is believed that the present invention will be used most widely with drugs whose bioavailability and/or absorption properties can be enhanced by use of the permeation enhancer of the present invention. It is believed also that the present invention can be used to a particularly good effect by combining the permeation enhancer of the present invention with a drug that is ingested orally and absorbed relatively poorly in the gastrointestinal tract ("GIT"). Examples of such drugs are those that are known to have a relatively slow rate of membrane permeation such as, for example, Class III and Class IV drugs. Class III drugs are highly soluble in aqueous media with poor membrane permeability. Class IV drugs have low water solubility and low permeability.

Representative drugs in these classifications include, for example organic and inorganic therapeutic agents in the range of up to 400 daltons (the so called "small molecule" drugs) in proteins, peptides, vaccines, antigens, oligomers and polymers of ribonucleic acid (RNA) or deoxyribonucleic acid (DNA) or mimetics thereof including oligonucleotides and polynucleotides composed of naturally-ocurring nucleobases, sugars and covalent inter-nucleoside (backbone) linkages as well as non-naturally-occurring portions which function similarly. Modified or substituted oligonucleotides and polynucleotides are often preferred over native forms because of desirable properties such as, for example, enhanced cellular uptake, enhanced affinity for nucleic acid targets and increased stability in the presence of nucleases. U.S. Pat. No. 6,379,960 teaches various suitable modifications and substitutions to oligonucleotides and polynucleotides.

Specific examples of drugs include "small molecule" drugs, for example, furoseamide, low molecular weight (LMW) heparin, nucleotides, peptides and protein such as insulin, growth hormone, calcitonin, enalaprilate, acyclovir, leuprolide acetate, antisense oligonucleotides, ribozymes, external guide sequence (EGS) oligonucleotides (oligozymes), and short catalytic RNAs or catalytic oligonucleotides which hybridize to a target nucleic acid and modulate its expression. It will be appreciated that the aforementioned list of drugs includes examples of hydrophilic drugs and macro-molecular drugs.

The drug can be in any suitable form, for example, in crystalline or amorphous form and in solid, liquid, or gel form, for example, in the form of nano particles and micro particles or in larger particle-size form. In addition, the drug can be present in the composition in a time-release form.

The composition of the present invention comprises a pharmaceutically effective amount of the drug, that is, an amount that is effective in achieving the desired prophylactic, therapeutic or diagnostic effect in the patient. It should be appreciated that the amount of drug comprising the composition will depend on various factors, including, for example, the particular drug used, the nature of the condition to be treated, the dosage form used and the nature of the patient.

Similarly, the enhancer compound contained in the composition of the present invention is present in an amount that is effective in increasing the bioavailability and/or absorption properties of the drug. The amount of enhancer in the composition will depend on various factors, including, for example, the particular drug(s) used, the amount of drug(s) employed, the dosage form selected, the particular enhancer compound used, the optical purity of the enhancer compound used, that is, whether it is used in the form of a pure isomer or as a partially or completely racemic mixture the type and amount of other enhancer compounds present. It is believed that, for most applications, the composition will comprise a drug: enhancer compound weight ratio of about 1:1000 to about 99:1. In most cases the ratio will be between about 1:5 and about 1:10. This ratio range is given for guideline purposes, with the understanding that ratios of drug to enhancer outside of this range may be used depending on the various factors mentioned above.

The composition of the present invention comprises optionally a vehicle, the nature of which will depend on the form of the composition. The composition can be used in any suitable form, for example, in the form of a granulate, solid, semi-solid, solution, suspension, tablet, capsule, inhalant, suppository or enema. The tablets and capsules can be in the form, for example, of delayed release, sustained release, or immediate release systems. It is believed that the composition of the present invention will be used most widely in solid oral dosage form.

The term "vehicle" is used broadly to include various types of pharmaceutically acceptable ingredients that can comprise the composition other than the drug and enhancer constituents of the composition. Examples of vehicles include fillers, diluents, excipients and materials, which have an effect on the release properties of the drug, or on the enhancer compound(s), that is, control-release materials. Examples of fillers and diluents include lactose, mannitol, dextrose, and microcrystalline cellulose vegetable oils, and glycerides. Examples of excipients include phosphate and citrate salts, magnesium stearate, silica, and binders such as hydroxypropyl methylcellulose, polyvinylpyrrolidone, and starch. Examples of control-release materials include enteric polymers, hydroxypropyl methylcellulose.

The amount of the various classes of constituents that comprise the carrier can be selected by the user to achieve the desired effects.

The examples below are illustrative of the present invention and compare the present invention to prior art compositions.

EXAMPLES

Example 1

LMW Heparin Composition including Sodium 2-hexyldecanoate

The performance characteristics of the branched chain permeation enhancer, sodium-2-hexyldecanoate, is compared with the performance of the straight chain sodium carboxylic acid, the sodium salt of capric acid, in a study of the intestinal absorption of Low Molecular Weight (LMW) heparin (parnaparin) when administered by intra-duodenal cannula to the conscious rat model.

The comparison is carried out using a non-randomized, parallel group design, and the animals used are male Wistar rats (25) in the 250-350 g-weight range (n=7 for each formulation). Animals are surgically implanted while under anesthesia with a duodenal cannula and a venous jugular vein) catheter for formulation administration and blood sampling respectively. The rats are allowed to recover for at least one day prior to dose administration. LMW heparin (Fluxum parnaparin-mean molecular weight 4000-4500 Dalton) formulations as described below are prepared in a phosphate buffer saline (0.01 M, pH 7.4) and are administered as a bolus (0.3 ml) into the duodenum. Blood samples are taken from the jugular vein at the following time intervals: 0 (pre-dose) 5, 10, 15, 30, 45, 60, 120, 180, 240 and 360 minutes. The samples are collected into epindorfs containing trisodium citrates and plasma is separated by centrifugation at 3000 rpm for 15 minutes. Plasma samples are stored at −20° C. until analysis. Samples are analyzed using Chromogenix Coatest® Heparin Kit and results expressed as antifactor Xa activity (IU/ml). The relative bioavailability (i.e. relative to a subcutaneous does of heparin 250 IU per animal) is calculated from the areas under the curve obtained from plasma antifactor Xa concentration-time profiles.

Compositions were administered to treatment groups, as shown in Table 1, below.

TABLE 1

| Group No. | Treatments |
| --- | --- |
| 1 | 1000IU LMWH (Parnaparin) + 17.5 mg Enhancer (1) + 17.5 mg C10 (2) (ID) |
| 2 | 1000IU LMWH (Parnaparin) + 35 mg Enhancer (ID) |
| A* | 1000IU LMWH (Parnaparin) (ID) |
| B* | 1000IU LMWH (Parnaparin) + 35 mg C10 (ID) |

*Nominally assigned treatments A and B for comparison purposes In the chart above, ID is intraduodenal, enhancer (1) is sodium-2-n-hexyl-decanoate, and C10 (2) is sodium caprate.

The pharmacokinetic measurements (mean±SD) are presented in Table 2, below.

TABLE 2

| | Treatments | | | |
| --- | --- | --- | --- | --- |
| PK Parameters | Treatment 1 1000IU LMWH (Parnaparin) + 17.5 mg Enhancer + 17.5 mg C10 (ID) | Treatment 2 1000IU LMWH (Parnaparin) + 35 mg Enhancer + 0 mg C10 (ID) | Treatment A* 1000IU LMWH (Parnaparin) (ID) | Treatment B* 1000IU LMWH (Parnaparin) + 0 mg Enhancer 35 mg C10 (ID) |
| % $F_{rel}$ | 5.45 ± 1.43 | 7.52* ± 3.27 | 0.37 ± 0.66 | 3.06 ± 3.14 |
| AUC (IU/ml · h) | 3.85 ± 1.01 | 5.31* ± 2.31 | 0.26 ± 0.47 | 2.16 ± 2.22 |
| Cmax (IU/ml) | 3.21 ± 0.77 | 2.51 ± 0.78 | 0.30 ± 0.38 | 1.61 ± 1.37 |

% $F_{rel}$ = % relative bioavailability.

The results of a statistical analysis of the above data is presented below, in Table 3, based on the % bioavailability and in Table 4, based on the differences in the peak serum concentration observed.

TABLE 3

BASED ON % BIOAVAILABILITY & AUC

| | |
| --- | --- |
| Treatment A versus Treatment B | Not significant (P > 0.05) |
| Treatment A versus Treatment 1 | Significant (P < 0.001) |
| Treatment A versus Treatment 2 | Significant (P < 0.01) |
| Treatment B versus Treatment 1 | Not significant (P > 0.05) |
| Treatment B versus Treatment 2 | Significant (P < 0.05) |
| Treatment 1 versus Treatment 2 | Not significant (P > 0.05) |

TABLE 4

BASED ON DIFFERENCES IN CMAX

| | |
| --- | --- |
| Treatment A versus Treatment B | Not significant (P > 0.05) |
| Treatment A versus Treatment 1 | Significant (P < 0.001) |
| Treatment A versus Treatment 2 | Significant (P < 0.01) |
| Treatment B versus Treatment 1 | Significant (P > 0.05) |
| Treatment B versus Treatment 2 | Not significant (P > 0.05) |
| Treatment 1 versus Treatment 2 | Not significant (P > 0.05) |

Table 3 shows that the bioavailability of LMW heparin dosed to animals without any permeation enhancers is very low (less than 0.5%). This however, significantly improved when the drug dosed is combined with a permeation enhancer. The highest bioavailability is observed when heparin is dosed with the permeation enhancer sodium 2-n-hexyl-decanoate. The enhancement of bioavailability with this branched chain compound is unexpectedly greater that that achieved with the straight chain carboxylic acid, sodium caprate. This unexpected increase is not only related to the increase in antifactor Xa plasma peak but also to a significant increase in the overall area under the curve as outlined by the differences in AUC.

More specifically, the relative bioavailability following the administration of 1000IU parnaparin (ID) is 0.37±0.66%. When 1000IU parnaparin is co-administered with 35 mg C10 (sodium caprate), the resultant relative bioavailability is 3.06±3.14%. When 1000IU parnaparin is co-administered with 17.5 mg branched chain enhancer and 17.5 mg C10 (sodium caprate), the resultant relative bioavailability is 5.45±1.43%. The highest relative bioavailability observed follows the administration of 1000IU parnaparin+35 mg branched chain enhancer i.e. 7.52±3.27%.

Table 4 shows that the enhancer of the present invention improves the absorption of LMW heparin from the intestine.

In conclusion, the branched chain enhancer compound, sodium 2-n-hexyl-decanoate, results in a higher and less variable LMWH bioavailability than when the straight chain C10 compound (sodium caprate) alone is co-administered with LMWH (parnaparin). Although the binary mix of sodium-2-n-hexyl-decanoate and C10 (sodium caprate) was less bioavailable than the formulation including sodium-2-n-hexyl-decanoate alone, treatment with the mixed formulation results in the least variable bioavailability.

Example 2

LMW Heparin Composition including Sodium 2-n-octyl-dodecanoate

The performance characteristics of the permeation enhancer compound, sodium-2-n-octyl-dodecanoate, is compared with the performance of the straight chain sodium carboxylic acid, sodium caprate, in a study of the intestinal absorption of LMW heparin (parnaparin) when administered by intra-duodenal cannula to the conscious rat model.

The comparison is carried out using a non-randomized, parallel group design, and the animals used are male Wistar rats (25) in the 250-350 g-weight range (n=7 for each formulation). Animals are surgically implanted while under anesthesia with a duodenal cannula and a venous (jugular vein) catheter for formulation administration and blood sampling respectively. The rats are allowed to recover for at least one day prior to dose administration. LMW heparin (Fluxum parnaparin-mean molecular weight 4000-4500 Dalton) formulations as described below are prepared in a phosphate buffer saline (0.01 M, pH 7.4) and are administered as a bolus (0.3 ml) into the duodenum. Blood samples are taken from the jugular vein at the following time intervals: 0 (pre-dose) 5, 10, 15, 30, 45, 60, 120, 180, 240 and 360 minutes. The samples are collected into epindorfs containing trisodium citrates and plasma is separated by centrifugation at 3000 rpm for 15 minutes. Plasma samples are stored at −20° C. until analysis. Samples are analyzed using Chromogenix Coatest® Heparin Kit and results expressed as antifactor Xa activity (IU/ml). The relative bioavailability (i.e. relative to a subcutaneous does of heparin 250 IU per animal) is calculated from the areas under the curve obtained from plasma antifactor Xa concentration-time profiles.

The formulations tested and the measurements of LMW heparin bioavailability and plasma peak after administration of said formulations are described in Table 5, below. The relative bioavailability (i.e. relative to a subcutaneous does of heparin 250 IU per animal) is calculated from the areas under the curve obtained from plasma antifactor Xa concentration-time profiles.

TABLE 5

| Formulations | Plasma peak (IU/ml) | Bioavailability (%) |
| --- | --- | --- |
| LMW heparin (1000 LU) + 35 mg sodium caprate | 2.16 ± 2.22 | 3.06 ± 3.14 |
| LMW heparin (1000 IU) 24.5 mg sodium caprate and 10.5 mg sodium 2-n-octyl-dodecanoate | 4.95 ± 2.21* | 6.69 ± 2.98* |

*P = 0.039. Results in above table are expressed as mean ± SD.

The bioavailability of LMW heparin dosed to animal without any permeation enhancer compound is very low (less than 0.4%). This however, significantly improved when the drug is dosed with the above formulations. The highest bioavailability is observed when LMW heparin was dosed with the permeation enhancer, sodium 2-n-octyl-dodecanoate. This enhancer system is not fully soluble in phosphate buffer saline; therefore it is administered in combination with straight chain carboxylate, sodium caprate, to improve solubility.

Example 3

Antisense Oligonucleotide

Composition including Sodium 2-n-octyl-dodecanoate

Compositions comprising sodium caprate and an antisense compound with and without an enhancer compound of the present development, sodium 2-n-octyl-dodecanoate were administered to animals to demonstrate the enhanced bioavailability of macromolecular compounds for example, oligo- and polynucleotides, afforded by the enhancer compounds of the present development. The ratio of enhancer and antisense compounds in the compositions is shown in Table 6.

Antisense oligonucleotides are synthesized by solid phase organic synthesis using appropriately protected synthons. Reversed phase chromatography was used to purify the antisense oligonucleotide, which has then deprotected and lyophilized.

The antisense oligonucleotide used is a 2'-O-(2-methoxyethyl) modified phosphorothioate oligonucleotide containing a 10-base 2' deoxy gap, also referred to as a 5-10-5 MOE gapmer, with 2' MOE modification of only the five nucleotides at the 3' and 5' termini of the oligonucleotide wherein each of the 19 inter-nucleotide linkages is an O,O-linked phosphorothioate. In addition, all cytosines are modified to by 5-methylcytosines. The 2' MOE modification makes an oligonucleotide more resistant to nuclease degradation, thereby improving both its RNA binding affinity and increasing its half life. This antisense oligonucleotide targets human TNF-α to treat inflammatory disorders, such as rheumatoid arthritis. This antisense oliconculeotide has a sequence of:
GCT GAT TAG AGA GAG GTC CC The compositions were compared by administering them in solution form through a catheter to test subjects. A jejunal catheter is surgically implanted in six male rhesus monkeys (3-5 years, 3-5 Kg) under anesthesia. The catheters are attached to a subcutaneous access port to allow dosing through the port into the jejunum. The animals are allowed to recover at least 7 days prior to dosing. Animals were fasted overnight prior to dosing and fed 2 hours post-dosing. Test formulations are prepared in water and are dosed to animals as a bolus (0.5 ml/kg) in a cross-over study design with a one week wash out period between each dose. Whole blood samples are taken from the femoral vein (other than the dosing site for intravenous administration) at the following time intervals: 0 (pre-dose) 2, 5, 10, 20, 30, 45, 60, 90, 120, 180, 240 and 360 minutes for intravenous dose and at 0 (pre-dose), 5, 15, 30, 45, 60, 90, 120, 150, 180, 240, 360 and 480 minutes for intra-jejunal doses. The samples are collected in EDTA-containing tubes and centrifuged in a refrigerated centrifuge (2-8° C.) to obtain plasma that is stored at −70° C. until analysis. The antisense oligonucleotide is detected by anion-exchange chromatography.

The formulations and the measurements of bioavailability, Tmax and plasma peak of antisense oligonucleotide after administration of formulations are described in the chart below. The bioavailability (i.e. relative to an intravenous dose) is calculated from the areas under the curve obtained from plasma oligonucleotide concentration-time profiles.

TABLE 6

| PK parameters | Antisense Oligonucleotide (10 mg/kg) Sodium caprate (50 mg/kg) | Antisense Oligonucleotide (10 mg/kg) Sodium 2-n-octyl-dodecanoate (15 mg/kg) + Sodium caprate (35 mg/kg) |
| --- | --- | --- |
| Peak plasma (g/ml) | 2.7 ± 1.5 | 8.7 ± 3.8* |
| Tmax (min) | 19 ± 12 | 30 ± 9 |
| AUC (g · min/ml) | 127 ± 8.7 | 451 ± 224* |
| % Bioavailability | 3.0 ± 2.1 | 10.8 ± 54* |

Results of above table are expressed as mean ± SD (n = 6), AUC = area under concentration-time curve, $T_{max}$ = time to reach peak plasma concentration; *p < 0.05.

The antisense oligonucleotide has poor permeability when administered to monkeys orally or intra-intestinally without any permeation enhancer systems. This bioavailability is significantly improved when the drug is dosed with a permeation enhancer. The highest bioavailability is observed with compositions including the permeation enhancer sodium 2-n-octyl-dodecanoate, in which bioavailability ranged from 5.2% to 18.2%. The enhancement of bioavailability with the branched chain enhancer compound relative to the straight chain sodium caprate alone is not only related to the increase in plasma peak but also to a significant increase in the overall area under the curve. The bioavailability achieved with compositions containing only the straight chain carboxylic acid salt, sodium caprate, ranged from 1.0% to 6.2%, a significantly reduced permeation enhancing effect.

Next is described the preparation of tablets containing heparin (Examples 4 and 5) and antisense oligonucleotide (Example 6).

Example 4

Sustained Release Heparin Tablets

A powder suitable for pressing into tablets will be prepared by blending in a blender 14.1 g of heparin, 19.47 g of sodium 2-n-octyl-dodecanoate, 45.43 g of sodium caprate, 20.0 g of hydroxypropylmethyl cellulose, and 0.5 g of each of silica and magnesium stearate. The powder is blended until homogeneous. Tablets which provide sustained release of heparin can be prepared by pressing the powder in a tablet press with sufficient pressure to form a cohesive tablet. The tablets may be enterically coated by applying an enteric coating composition to them using a side vented coating pan.

A suitable enteric coating composition will be formed by mixing 49.86 g of Eudragit L® 12.5, 1.26 g diethyl phthalate, 43.33 g isopropyl alcohol, 2.46 g of talc and 3.06 g of water.

Example 5

Instant Release Heparin Tablets

A powder suitable for compressing into tablets will be prepared by blending in a blender 6.57 g of sodium 2-n-octyl-dodecanoate, 59.13 g of sodium caprate, 13.3 g of heparin, 20 g of mannitol and 0.5 g of each of magnesium stearate and silica. The powder is blended until homogeneous.

Tablets which provide an instant release of heparin will be prepared by pressing the powder in a tablet press with sufficient pressure to provide a cohesive tablet. The tablets may be enterically coated using the procedure designed above in Example 4.

Example 6

Tablets Containing an Antisense Oligonucleotide

A granulate suitable for pressing into a tablet will be prepared by spray granulation of a powder comprising a homogeneous blend of the antisense oligonucleotide, sodium 2-n-octyl-dodeconoate, sodium caprate and suitable pharmaceutical excipients.

The granulate is prepared by blending in a blender 15 g of the antisense oligonucleotide of Example 3, 58.5 g of sodium caprate, 6.5 g of 2-n-octyl-dodecanoate, 12.5 g of Avicel ph101, 5 g of PVP K-30 solids. The powder blend is granulated by spray drying using an aqueous solution containing 5% of PVP K-30 solids until a homogeneous granulate is obtained.

Thus obtained, 53.5 g of the granulate is blended in a blender with 40 g of mannitol, 5 g of Polyplasdone XL, 1 g of Aerosil 200 and 0.5 g of stearic acid until a homogeneous admixture is obtained.

Tablets providing an instant release of the antisense oligonucleotide can be prepared by pressing the admixture in a tablet press with sufficient pressure to obtain a cohesive tablet. The tablets are enterically coated using the procedure designed above in Example 4.

Example 7 describes the preparation of a semi-solid comprising an enhancer of the present invention and a peptide drug, leuprolide acetate.

Example 7

Semi-solid Containing Leuprolide Acetate

A composition comprising the present invention enhancer compound 2-n-octyl-dodecanoate and leuprolide acetate can be provided in a semi-solid form.

The semi-solid can be prepared by blending 1 g of leuprolide acetate, 1 g of colloidal silicon dioxide, 10 g of sodium 2-n-octyl-dodecanoate, 62 g of Capmul MCM 8, 4 g of triolein, 3 g of polyoxyethylene sorbitan mono-oleate and 19 g of stearoyl Macrogol-32 glyceride.

The semi-solid is filled in hard gelatin capsules and maybe coated using a suitable enteric coating solution.

From the above description, it should be appreciated that the present invention provides a method of drug delivery which overcomes the natural barrier properties of bodily membranes and skin in such a way that bioavailability of the drug is improved significantly and pharmaceutically effective amounts of drugs can be provided at a sustainable rate over an extended period of time. Although enhancers of the present invention are useful in applications involving drug delivery across the skin and various mucous and other cellular membranes, they are especially effective in improving the bioavailability of drugs that are ingested orally and then absorbed in the GI tract.

While not wishing to be bound by a scientific theory regarding the mechanism by which the drug delivery system of the present invention functions, it is believed that the drug is transported through the skin or membrane barrier by the chemical processes of diffusion and capillary action. For example, the resistance or barrier property of the skin or membrane is due at least in part to the highly ordered intercellular lipid structure of the stratum corneum, a phospholipid bilayer membrane. The permeation enhancer may disrupt and reduce the orderly structure of the stratum corneum, thus making the cell structure more fluid. This allows higher rates of drug permeation by diffusion. Concurrently with increased diffusion rates (as result of disruption of the stratum corneum), the permeation enhancer causes an increase in the surface activity of the drug molecule itself, thus effecting a faster movement of the drug through the skin structure.

Drug permeation rates are influenced by factors related both to the membrane and to the drug itself. With respect to the membranes, the individual cellular units are a major factor in controlling the permeation rate of a drug. The plasma layer surrounding each cell is comprised of phospholipids having alternating hydrophilic and hydrophobic layers which serve a protective function, but which also pose a barrier to many drugs. The nature of this barrier may vary among the membranes of the body. Drugs generally vary in chemical properties such as solubility, polarity, and molecular size and, therefore, have variable rates of diffusion through bodily membranes. Because each combination of drug and target membrane within the body presents a unique environment for permeation, the pathways to achieving adequate bioavailability levels are typically complex and unpredictable. It is believed that the enhancers of the present invention provide an improved solution to the problem of effective permeation by enabling one to select enhancers having proper chain length, branch point location, acid group number, and position on the various chains and to optimize the formulation of compositions which are particularly effective for delivering drugs.

We claim:

1. A pharmaceutical composition comprising:
   (a) a hydrophilic or macromolecular drug having poor membrane permeability;
   (b) a branched chain permeation enhancer comprising an acid functional group-containing compound of Formula I in which at least 50% of the total number of acid functional groups present have been reacted with a base, the compound of Formula I comprising:

Formula I wherein,
Q is a partially or completely neutralized —COOH functional group,
$R_1$ is $C_{6-8}$ alkyl,
$R_2$ is $C_{8-10}$ alkyl,
and wherein the permeation enhancer is present in an amount sufficient to increase the bioavailability of the drug upon transdermal or transmucosal administration to a patient; and
(c) optionally, other pharmaceutically acceptable ingredients.

2. The pharmaceutical composition of claim 1 wherein said permeation enhancer is a compound of Formula I, wherein:
Q is —COONa
$R_1$ is —$C_6$ straight chain alkyl, and
$R_2$ is —$C_8$ straight chain alkyl.

3. The pharmaceutical composition of claim 1 wherein said permeation enhancer is a compound of Formula I wherein:
Q is —COONa
$R_1$ is —$C_8$ straight chain alkyl, and
$R_2$ is —$C_{10}$ straight chain alkyl.

4. The pharmaceutical composition of claim 1 wherein said drug is selected from the group consisting of proteins, peptides, and antigens.

5. The pharmaceutical composition of claim 1 wherein said drug is heparin.

6. The pharmaceutical composition of claim 1 wherein the hydrophilic or macromolecular drug having poor membrane permeability is a Class III or a Class IV drug.

7. The pharmaceutical composition of claim 6 wherein the Class III or Class IV drug is selected from the group consisting of furoseamide, low molecular weight heparin, nucleotides, peptides, proteins, growth hormone, calcitonin, enalaprilate, acyclovir, leuprolide acetate, antisense oligonucleotides, ribozymes, external guide sequence oligonucleotides, and RNAs.

8. The pharmaceutical of claim 1, wherein said pharmaceutical is in a form for transmucosal delivery and wherein the permeation enhancer is present in an amount sufficient to increase the bioavailability of the drug upon transmucosal administration to a patient.

9. The pharmaceutical composition of claim 8, wherein the drug is a Class III or a Class IV drug.

10. The pharmaceutical composition of claim 8, wherein said form for transmucosal administration is selected from the group consisting of: a form for aerosol delivery of the drug to the nose or lungs; and a form for oral ingestion of the drug followed by permeation through the gastrointestinal wall.

11. The pharmaceutical composition of claim 9 wherein the Class III or Class IV drug is selected from the group consisting of furoseamide, low molecular weight heparin, nucleotides, peptides, proteins, growth hormone, calcitonin, enalaprilate, acyclovir, leuprolide acetate, antisense oligonucleotides, ribozymes, external guide sequence oligonucleotides, and RNAs.

12. The pharmaceutical composition of claim 1, wherein said composition is in a form for transdermal delivery and wherein the permeation enhancer is present in an amount sufficient to increase the bioavailability of the drug upon transdermal administration to a patient.

13. The pharmaceutical composition of claim 12, wherein the hydrophilic or macromolecular drug having poor membrane permeability is a Class III or a Class IV drug.

14. The pharmaceutical composition of claim 12, wherein said form for transdermal administration is selected from the group consisting of: a solid form; a liquid form; and a gel form, and wherein said composition is suitable for application through the skin by use of a transdermal patch.

15. The pharmaceutical composition of claim 13 wherein the Class III or Class IV drug is selected from the group consisting of furoseamide, low molecular weight heparin, nucleotides, peptides, proteins, growth hormone, calcitonin, enalaprilate, acyclovir, leuprolide acetate, antisense oligonucleotides, ribozymes, external guide sequence oligonucleotides, and RNAs.

16. A method of providing for enhanced uptake of a hydrophilic or macromolecular drug having poor membrane permeability in the gastrointestinal tract of an animal, the method comprising providing an oral dosage form containing a therapeutically effective amount of the pharmaceutical composition of claim 12, wherein said composition is in a form for transmucosal delivery by permeation through the gastrointestinal wall.

17. A method of administering a hydrophilic or macromolecular drug having poor membrane permeability to a patient in need thereof comprising administering to the patient the pharmaceutical composition of claim 1 containing said drug and said permeation enhancer of Formula I wherein the permeation enhancer is present in an amount sufficient to increase the bioavailability of the drug upon transdermal or transmucosal administration to a patient.

18. The method of claim 17 wherein Q is —COONa, $R_1$ is —$C_6$ straight chain alkyl, and $R_2$ is —$C_8$ straight chain alkyl.

19. The method of claim 17 wherein Q is —COONa, $R_1$ is —$C_8$ straight chain alkyl, and $R_2$ is —$C_{10}$ straight chain alkyl.

20. A method of administering a hydrophilic or macromolecular drug having poor membrane permeability to a patient in need thereof comprising administering to the patient the composition of claim 8 containing said drug and said permeation enhancer wherein the permeation enhancer is present in an amount sufficient to increase the bioavailability of the drug upon transmucosal administration to a patient.

21. A method of administering a hydrophilic or macromolecular drug having poor membrane permeability to a patient in need thereof comprising administering to the patient the composition of claim 12 containing said drug and said permeation enhancer wherein the permeation enhancer is present in an amount sufficient to increase the bioavailability of the drug upon transdermal administration to a patient.

* * * * *